United States Patent [19]

Sutherland et al.

[11] Patent Number: 4,910,219

[45] Date of Patent: Mar. 20, 1990

[54] MACROLIDE COMPOUNDS

[75] Inventors: Derek R. Sutherland, Chalfont St Giles; John B. Ward, Bushey; Neil Porter, Pinner; Hazel M. Noble, Burnham; Richard A. Fletton, Ruislip; David Noble, Burnham, all of England

[73] Assignee: American Cyanamid Company, Stamford, Conn.

[21] Appl. No.: 24,669

[22] Filed: Mar. 11, 1987

[30] Foreign Application Priority Data

Mar. 12, 1986 [GB] United Kingdom ............... 8606108

[51] Int. Cl.$^4$ ............................................. A61K 31/71
[52] U.S. Cl. ...................................... 514/450; 549/264
[58] Field of Search .......................... 549/264; 514/450

[56] References Cited

U.S. PATENT DOCUMENTS

| | | | |
|---|---|---|---|
| 4,201,861 | 5/1980 | Mrozik et al. | 536/7.1 |
| 4,289,760 | 9/1981 | Mrozik et al. | 536/7.1 |
| 4,423,209 | 12/1983 | Mrozik | 549/264 |
| 4,530,921 | 7/1985 | Mrozik | 549/264 |
| 4,547,520 | 10/1985 | Ide et al. | 549/264 |
| 4,579,864 | 4/1986 | Linn et al. | 549/264 |
| 4,696,922 | 9/1987 | Sturm et al. | 549/264 |

FOREIGN PATENT DOCUMENTS 170006 2/1986 European Pat. Off. .

Primary Examiner—Glennon H. Hollrah
Assistant Examiner—Ba K. Trinh
Attorney, Agent, or Firm—Bacon & Thomas

[57] ABSTRACT

Compounds are described of the formula

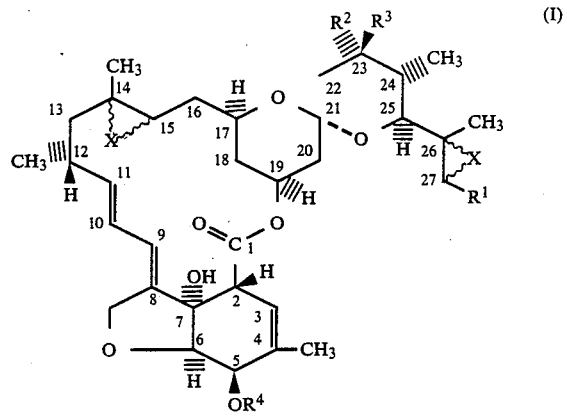

and salts thereof, wherein $R^1$ is methyl, ethyl or isopropyl;

$R^2$ is —H, —OH or substituted —OH and $R^3$ is —H, or $R^2$ and $R^3$ together with the carbon atom to which they are attached represent C=CH$_2$, C=O or C=NOR$^6$ (where $R^6$ is —H, alkyl or alkenyl and the C=NOR$^6$ is in the E configuration);

OR$^4$ is as defined above for OR$^5$ and one of the symbols X represents an epoxide oxygen atom and the other represents an epoxide oxygen atom or a carbon-carbon bond.

These compounds may be used for controlling insect, acarine, nematode or other pests.

8 Claims, No Drawings

MACROLIDE COMPOUNDS

This invention relates to novel antibiotic compounds and to processes for their preparation.

In our United Kingdom Patent Specification No. 2166436A we describe the production of Antibiotics S541 which may be isolated from the fermentation products of a novel Streptomyces sp. Said antibiotic compound can also be produced by fermentation of microorganism Streptomyces sp. deposited in the Northern Regional Research Center under Accession No. NRRL 15773 as disclosed in U.S. Ser. No. 617,649, filed June 5, 1984, now U.S. Pat. No. 4,869,901.

We have now found a further group of compounds with antibiotic activity which may be prepared by chemical modification of Antibiotics S541. The novel compounds of the invention have antibiotic activity and/or are of use as intermediates in the preparation of other active compounds.

Thus in one aspect, the invention particularly provides the compounds of formula (I):

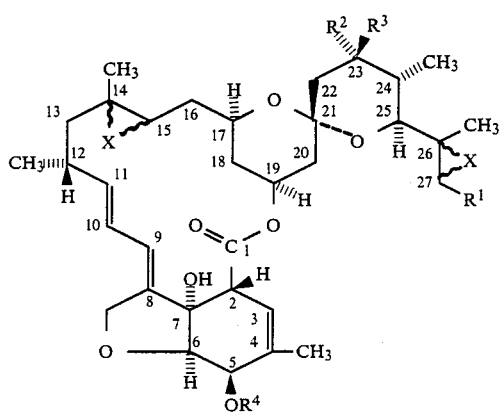

and salts thereof, wherein $R^1$ represents a methyl, ethyl or isopropyl group; $R^2$ represents a hydrogen atom or a group $OR^5$ (where $OR^5$ is a hydroxyl group or a substituted hydroxyl group having up to 25 carbon atoms) and $R^3$ represents a hydrogen atom, or $R^2$ and $R^3$ together with the carbon atom to which they are attached represent $>C=CH_2$, $>C=O$ or $>C=NOR^6$ (where $R^6$ represents a hydrogen atom, a $C_{1-8}$ alkyl group or a $C_{3-8}$ alkenyl group and the group $>C=NOR^6$ is in the E configuration); $OR^4$ is as defined above for $OR^5$ and one of the symbols $\sim X\sim$ represents an epoxide oxygen atom and the other represents an epoxide oxygen atom or a carbon-carbon bond.

It will be appreciated that the configuration of the methyl group at the 14-position will remain constant whether an epoxide group or a double bond is present at the 14-position. Thus the epoxide group is introduced with a retention of the overall stereochemistry at the appropriate carbon atoms.

Similarly at the 26, 27-position the stereochemistry of the carbon atoms is retained.

When the compounds of formula (I) are to be used as intermediates, one or both of the groups $R^2$ and $-OR^4$ will often be a protected hydroxy group and the invention particularly includes such protected compounds.

When the groups $R^2$ or $OR^4$ in compounds of formula (I) are substituted hydroxyl groups they may be the same or different and may represent acyloxy groups [e.g. a group of the formula $-OCOR^7$, $-OCO_2R^7$ or $-OCSOR^7$ (where $R^7$ is an aliphatic, araliphatic or aromatic group, for example an alkyl, alkenyl, akynyl, cycloalkyl, aralkyl or aryl group)], a formyloxy group, a group $-OR^8$ (where $R^8$ is as defined above for $R^7$), a group $-OSO_2R^9$ (where $R^9$ is a $C_{1-4}$ alkyl or $C_{6-10}$ aryl group), a silyloxy group, a cyclic or acyclic acetaloxy group, a group $OCO(CH_2)_nCO_2R^{10}$ (where $R^{10}$ is a hydrogen atom or a group as defined for $R^7$ above and n represents zero, 1 or 2) or a group $-OCONR^{11}R^{12}$ (where $R^{11}$ and $R^{12}$ may each independently represent a hydrogen atom or a $C_{1-4}$ alkyl group e.g. methyl).

Where $R^7$ or $R^8$ are alkyl groups, they may be for example $C_{1-8}$ alkyl groups e.g. methyl, ethyl, n-propyl, i-propyl, n-butyl, i-butyl, t-butyl or n-heptyl which alkyl groups may also be substituted. Where $R^7$ is a substituted alkyl group it may be substituted by, for example, one or more, e.g. two or three halogen atoms (e.g. chlorine or bromine atoms), or a carboxy, $C_{1-4}$ alkoxy (e.g. methoxy, ethoxy), phenoxy or silyloxy group. Where $R^8$ is a substituted alkyl group it may be substituted by a $C_{3-7}$ cycloalkyl e.g. cyclopropyl group.

Where $R^7$ or $R^8$ alkenyl or akynyl groups, they may be for example $C_{2-8}$ akenyl, e.g. allyl, or $C_{2-8}$ alkynyl groups.

Where $R^7$ or $R^8$ are cycloalkyl groups, they may be for example $C_{3-12}$ cycloalkyl. Thus $R^7$ may be for example a cyclopropyl, cyclobutyl, cyclopentyl or cyclohexyl group. $R^8$ may be for example a cyclopentyl group.

Where $R^7$ or $R^8$ are aralkyl groups, they preferably have 1 to 6 carbon atoms in the alkyl moiety and the aryl group(s) may be carbocyclic or heterocyclic and preferably contain 4-15 carbon atoms e.g. phenyl. Examples of such groups include $phenC_{1-6}alkyl$, e.g. benzyl or phenethyl groups.

Where $R^7$ or $R^8$ are aryl groups, they may be carbocyclic or heterocyclic and preferably have 4-15 carbon atoms, and may be for example a phenyl group.

When $R^2$ or $-OR^4$ is a group $-OSO_2R^9$, it may be for example a methylsulphonyloxy or p-toluenesulphonyloxy group.

Where $R^2$ or $-OR^4$ represents a cyclic acetaloxy group, it may for example have 5–7 ring members and may be for example a tetrahydropyranyloxy group.

When $R^2$ or $-OR^4$ represents a silyloxy group or $R^7$ contains a silyloxy substituent, the silyl group may carry three groups which may be the same or different, selected from alkyl, alkenyl, alkoxy, cycloalkyl, aralkyl, aryl and aryloxy groups. Such groups may be as defined above for $R^7$ and particularly include methyl, t-butyl and phenyl groups. Particular examples of such silyloxy groups are trimethylsilyloxy and t-butyldimethylsilyloxy.

Where $R^2$ or $OR^4$ represent a group $OCO(CH_2)_nCO_2R^{10}$, it may for example be a group $OCOCO_2R^{10}$ or $OCOCH_2CH_2CO_2R^{10}$ represents a hydrogen atom or $C_{1-4}$ alkyl (e.g. methyl or ethyl) group.

Compounds of formula (I) containing an acidic group may form salts with suitable bases. Examples of such salts include alkali metal salts such as sodium and potassium salts.

In the compounds of formula (I), the group $R^1$ is preferably as isopropyl group.

The group $OR^4$ in the compounds of formula (I) is preferably a methoxycarbonyloxy group, or more preferably an acetoxy, methoxy, or hydroxy group. In general, compounds of formula (I) in which $OR^4$ is a hydroxy group are particularly preferred.

As indicated previously, the compounds according to the invention may be of use as antibiotics and/or as intermediates for the preparation of other active compounds. When the compounds of the invention are to be used as intermediates, the $R^2$ and/or $—OR^4$ groups may be protected hydroxyl groups. It will be appreciated that such a group should have the minimum of additional functionality to avoid further sites of reaction and should be such that it is possible to selectively regenerate a hydroxyl group from it. Examples of protected hydroxyl groups are well known and are described, for example, in "Protective Groups in Organic Systhesis" by Theodora W. Greene. (Wiley-Interscience, New York 1981) and "Protective Groups in Organic Chemistry" by J. F. W. McOmie (Plenum Press, London, 1973). Examples of $R^2$ and $OR^4$ protected hydroxy groups include phenoxyacetoxy, silyloxyacetoxy, (e.g. trimethylsilyloxyacetoxy and t-butyldimethylsilyloxyacetoxy), and silyloxy such as trimethylsilyloxy and t-butyldimethylsilyloxy. Compounds of the invention containing such groups will primarily be of use as intermediates. Other groups such as acetoxy, may serve as protected hydroxyl groups, but may also be present in final active compounds.

Compounds of the invention have antibiotic activity e.g. antihelminthic activity, for example against nematodes, and in particular, anti-endoparasitic and anti-ectoparasitic activity.

The compounds of the invention are therefore of use in treating animals and humans with endoparasitic and/or ectoparasitic infections.

Ectoparasites and endoparasites infect humans and a variety of animals and are particularly prevalent in farm animals such as pigs, sheep, cattle, goats and poultry (e.g. chickens and turkeys), horses, rabbits, game-birds, caged birds, and domestic animals such as dogs, cats, guinea pigs, gerbils and hamsters. Parasitic infection of livestock, leading to anaemia, malnutrition and weight loss is a major cause of economic loss throughout the world.

Examples of genera of endoparasites infecting such animals and/or humans are Ancylostoma, Ascaridia, Ascaris, Aspicularis, Brugia, Bunostomum, Capillaria, Chabertia, Cooperia, Dictyocaulus, Dirofilaria, Dracunculus, Enterobius, Haemonchus, Heterakis, Loa, Necator, Nematodirus, Nematospiroides (Heligomoroides), Nippostrongylus, Oesophagostomum, Onchocerca, Ostertagia, Oxyuris, Parascaris, Strongylus, Strongyloides, Syphacia, Toxascaris, Toxocara, Trichonema, Trichostrongylus, Trichinella, Trichuris, Triodontophorus, Uncinaria and Wuchereria.

Examples of ectoparasites infecting animals and/or humans are arthropod ectoparasites such as biting insects, blowfly, fleas, lice, mites, sucking insects, ticks and other dipterous pests.

Examples of genera of such ectoparasites infecting animals and/or humans are Ambylomma, Boophilus, Chorioptes, Culliphore, Demodex, Damalinia, Dermatobia, Gastrophilus, Haematobia; Haematopinus, Haemophysalis, Hyaloma, Hypoderma, Ixodes, Linognathus, Lucilia, Melophagus, Oestrus, Otobius, Otodectes, Psorergates, Psoroptes, Rhipicephalus, Sarcoptes, Stomoxys and Tabanus.

The compounds according to the invention have been found to be effective both in vitro and in vivo against a range of endoparasites and ectoparasites. The antibiotic activity of compounds of the invention may, for example, be demonstrated by their activity against free living nematodes e.g. *Caenorhabiditis elegans*. In particular, we have found that compounds of the invention are active in vivo against parasitic nematodes such as *Nematospiroides dubius* and *Nippostrongylus braziliensis*.

Compounds of the invention are also of use as antifungals, for example, against strains of Candida sp. such as *Candida albicans* and *Candida glabrata* and against yeast such as *Saccharomyces carlsbergensis*.

Compounds of the invention are also of use in combating insect, acarine and nematode pests in agriculture, horticulture, forestry, public health and stored products. Pests of soil and plant crops, including cereals (e.g. wheat, barley, maize and rice), cotton, tobacco, vegetables (e.g. soya), fruit (e.g. apples, vines and citrus) as well as root crops (e.g. sugarbeet, potatoes) may usefully be treated. Particular examples of such pests are fruit mites and aphids such as *Aphis fabae, Aulacorthum circumflexum, Myzus persicae, Nephotettix cincticeps, Nilparvata lugen, Panonychus ulmi, Phorodon humuli, Phyllocoptruta oleivora, Tetranychus urticae* and members of the gerera Trialeuroides; nematodes such as members of the genera Aphelencoides, Globodera, Heterodera, Meloidogyne and Panagrellus; lipidoptera such as Heliothis, Plutella and Spodoptera; grain weevils such as *Anthonomus grandis* and *Sitophilus granarius;* flour beetles such as *Tribolium castaneum;* flies such as *Musca domestica;* fire ants; leaf miners; *Pear psylla; Thrips tabaci;* cockroaches such as *Blatella germanica* and *Periplaneta americana* and mosquitoes such as *Aedes aegypti*.

According to the invention we therefore provide compounds of formula (I) as defined above, which may be used as antibiotics. In particular, they may be used in the treatment of animals and humans with endoparasitic, ectoparasitic and/or fungal infections and in agriculture, horticulture, or forestry as pesticides to combat insect, acarine and nematode pests. They may also be used generally as pesticides to combat or control pests in other circumstances, e.g. in stores, buildings or other public places or location of the pests. In general the compounds may be applied either to the host (animal or human or plants or vegetation) or a locus thereof or to the pests themselves.

Compounds of the invention may be formulated for administration in any convenient way for use in veterinary or human medicine and the invention therefore includes within its scope pharmaceutical compositions comprising a compound in accordance with the invention adapted for use in veterinary or human medicine. Such compositions may be presented for use in conventional manner with the aid of one or more suitable carriers or excipients. The compositions of the invention include those in a form especially formulated for parenteral (including intramammary administration), oral, rectal, topical, implant, ophthalmic, nasal or genito-urinary use.

The compounds according to the invention may be formulated for use in veterinary or human medicine by injection and may be presented in unit dose form, in ampoules, or other unit-dose containers, or in multidose containers, if necessary with an added preservative. The compositions for injection may be in the form of suspensions, solutions, or emulsions, in oily or aqueous vehicles, and may contain formulatory agents such as suspending, stabilising, solubilising and/or dispersing agents. Alternatively the active ingredient may be in sterile powder form for reconstitution with a suitable vehicle, e.g. sterile, pyrogen-free water, before use. Oily vehicles include polyhydric alcohols and their esters such as glycerol esters, fatty acids, vegetable oils such as arachis oil or cottonseed oil, mineral oils such as liquid paraffin, and ethyl oleate and other similar compounds. Other vehicles such as propylene glycol may also be used.

Compositions for veterinary medicine may also be formulated as intramammary preparations in either long acting or quick-release bases and may be sterile solutions or suspensions in aqueous or oily vehicles optionally containing a thickening or suspending agent such as soft or hard paraffins, beeswax, 12-hydroxy stearin, hydrogenated castor oil, aluminium stearates, or glyceryl monostearate. Conventional non-ionic, cationic or anionic surface active agents may be used alone or in combination in the composition.

The compounds of the invention may also be presented for veterinary or human use in a form suitable for oral administration, for example in the form of solutions, syrups or suspensions, or a dry powder for constitution with water or other suitable vehicle before use, optinally with flavouring and colouring agents. Solid compositions such as tablets, capsules, lozenges, pills, boluses, powder, pastes, granules, bullets or premix preparations may also be used. Solid and liquid compositions for oral use may be prepared according to methods well known in the art. Such compositions may also contain one or more pharmaceutically acceptable carriers and exicipients which may be in solid or liquid form. Examples of suitable pharmaceutically acceptable carriers for use in solid dosage forms include binding agents (e.g. pregelatinised maize starch, polyvinylpyrrolidone or hydroxypropyl methycellulose); fillers (e.g. lactose, micro-crystalline cellulose or calcium phosphate); lubricants (e.g. magnesium stearate, talc or slica); disintegrants (e.g. potato starch or sodium stach glycollate); or wetting agents (e.g. sodium lauryl sulphate. Tablets may be coated by methods well known in the art.

Examples of suitable pharmaceutically acceptable additives for use in liquid dosage forms include suspending agents (e.g. sorbitol syrup, methyl cellulose or hydrogenated edible fats); emulsifying agents (e.g. lecithin or acacia); non-aqueous vehicles (e.g. almond oil, oily esters or ethyl alcohol); and preservatives (e.g. methyl or propyl p-hydroxybenzoates or sorbic acid); stabilising and solubilising agents may also be includeed.

Pastes for oral administration may be formulated according to methods well known in the art. Examples of suitable pharmaceutically acceptable additives for use in paste formulations include suspending or gelling agents e.g. aluminium distearate or hydrogenated castor oil; dispersing agents e.g. polysorbates, non-aqueous vehicles e.g. arachis oil or oily esters; stabilising and solubilising agents. The compounds of the invention may also be administered in veterinary medicine by incorporation thereof into animals daily solid or liquid dietary intake, e.g. as part of the daily animal feed or drinking water.

The compounds of the invention may also be administered orally in veterinary medicine in the form of a liquid drench such as a solution, suspension or dispersion of the active ingredient together with a pharmaceutically acceptable carrier or excipient.

The compounds of the invention may also, for example, be formulated as suppositories e.g. containing conventional suppository bases for use in veterinary or human medicine or as pessaries e.g. containing conventional pessary bases.

Compounds according to the invention may be formulated for topical administration, for use in veterinary and human medicine, as ointments, creams, lotions, shampoos, powders, pessaries, sprays, dips, aerosols, drops (e.g. eye or nose drops) or pour-ons. Ointments and creams may, for example, be formulated with an aqueous or oily base with the addition of suitable thickening and/or gelling agents. Ointments for administration to the eye may be manufactured in a sterile manner using sterilised components. Pour-ons may, for example, be formulated for veterinary use in oils containing organic solvents, optionally with formulatory agents e.g. stabilising and solubilising agents.

Lotions may be formulated with an aqueous or oily base and will in general also contain one or more emulsifying agents, stabilising agents, dispersing agents, suspending agents, thickening agents, or colouring agents.

Powders may be formed with the aid of any suitable powder base. Drops may be formulated with an aqueous or non aqueous base also comprising one or more dispersing agents, stabilising agents, solubilising agents or suspending agents. They may also contain a preservative.

For topical administration by inhalation the compounds according to the invention may be delivered for use in veterinary or human medicine in the form of an aerosol spray presentation or an insufflator.

The compounds of the invention may be administered in combination with other pharmaceutically active ingredients.

The total daily dosages of compounds of the invention employed in both veterinary and human medicine will suitably be in the range 1–2000 μg/kg bodyweight, preferably from 50–1000 μg/kg and these may be given in divided doses, e.g. 1–4 times per day.

The compounds according to the invention may be formulated in any convenient way for horticultural or agricultural use and the invention therefore includes within its scope compositions comprising a compound according to the invention adapted for horticultural or agricultural use. Such formulations include dry or liquid types, for example dusts, including dust bases or concentrates, powders, including soluble or wettable powders, granulates, including microgranules and dispersible grauules, pellets, flowables, emulsions such as dilute emulsions or emulsifiable concentrates, dips such as root dips and seed dips, seed dressings, seed pellets, oil concentrates, oil solutions, injections e.g. stem injections, sprays, smokes and mists.

Generally such formulations will include the compound in association with a suitable carrier or diluent. Such carriers may be liquid or solid and designed to aid the application of the compound either by way of dispersing it where it is to be applied or to provide a formulation which can be made by the user into a dispersible preparation. Such formulations are well known in the art and may be prepared by conventional methods such as, for example by blending and/or grinding of the active ingredient(s) together with the carrier or diluent, e.g. solid carrier, solvent or surface active agent.

Suitable solid carriers, for use in the formulations such as dusts, granulates and powders may be selected from for example natural mineral fillers, such as diatomite, talc, kaolinite, montmorillonite prophyllite or attapuglite. Highly dispersed silicic acid or highly dispersed absorbent polymers may, if desired, be included in the composition. Granulated adsorptive carriers which may be used may be porous (such as pumice, ground brick, sepiolite or bentonite) or non-porous (such as calcite or sand). Suitable pregranulated materials which may be used and which may be organic or inorganic include dolomite and ground plant residues.

Suitable solvents for use as carriers or diluents include aromatic hydrocarbons, aliphatic hydrocarbons, alcohols and glycols or ethers thereof, esters, ketones, acid amides, strongly polar solvents, optionally epoxidized vegetable oils and water.

Conventional non-ionic, cationic or anionic surface-active agents. e.g. ethoxylated alkyl phenols and alcohols, alkali metal or alkaline earth metal salts of alkyl benzene sulphonic acids, lignosulphonic acids or sulphosuccinic acids or sulphonates of polymeric phenols which have good emulsifying, dispersing and/or wetting properties may also be used either alone or in combination in the compositions.

Stabilizers, anti-caking agents, anti-foaming agents, viscosity regulators, binders and adhesives, photostabilisers as well as fertilizers, feeding stimulants or other active substances may, if desired, be included in the compositions. The compounds of the invention may also be formulated in admixture with other insecticides, acaricides and nematicides.

In the formulations, the concentration of active material is generally from 0.01 to 99% and more preferably between 0.01% and 40% by weight.

Commercial products are generally provided as concentrated compositions to be diluted to an appropriate concentration, for example from 0.001 to 0.0001% by weight, for use.

According to a further aspect of the invention we provide a process for the preparation of the compounds of formula (I) as defined above which comprises reacting compounds of formula (II):

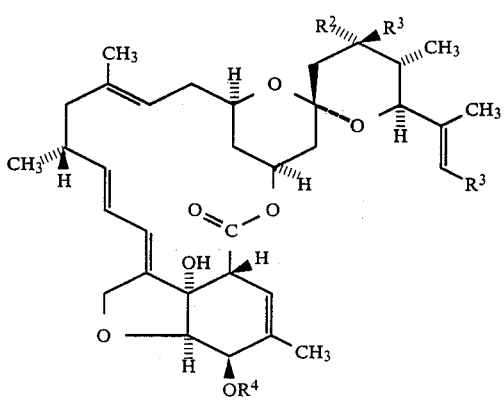

(where $R^1$, $R^2$, $R^3$ and $R^4$ are as previously defined) with an oxidising agent serving to convert a carbon-carbon double bond into an epoxide group, to form the desired compounds of formula (I).

Suitable oxidising agents include peracids and salts thereof for example peroxytrifluoroacetic acid, peroxybenzoic acid, peroxyacetic acid, m-chloropeoxybenzoic acid, and peroxyphthalic acid magnesium salt.

Suitable solvents for the reaction include alcohols, such as methanol; hydrocarbons, such as hexane; halogenated hydrocarbons, such as chloroform or methylene chloride; acetonitrile; cyclic ethers, such as tetrahydrofuran, or esters, such as ethyl acetate. Combinations of such solvents either alone or with water may also be used.

The quantity of epoxide-forming reagent may be approximately stiochiometric or in slight excess, e.g. 1 to 2.5 equivalents. It is often convenient to add the oxidising agent in portions and to monitor the reaction, e.g. by thin layer chromatography.

The reaction may conveniently be carried out at a temperature of from $-50°$ C. to $+50°$ C., preferably 0° to 30° C.

In general, a mixture of epoxides will be formed. Thus, a mixture of both mono-epoxides and the bis-epoxide will be formed and each epoxide group may be in either of the two possible configurations, although we have found that in general, the epoxidation is generally stereoselective. Separation can however readily be effected, for example using fractionation techniques such as chromatography (including high performance liquid chromatography) on a suitable support such as silica, a non-functional macroreticular adsorption resin for example cross linked polystyrene resins such as Amberlite XAD-2, XAD-4 or XAD-1180 resins (Rohm and Haas Ltd), or on an organic solvent-compatible cross-linked dextran such as Sephadex LH20 Amberlite XAD-2, XAD-4 or XAD-1180 resins (Rohm and Haas Ltd), or on an organic solvent-compatible cross-linked dextran such as Sephadex LH20 (Pharmacia UK Ltd), or, in the case of hplc, reverse phase supports such as hydrocarbon linked silica e.g. $C_{18}$-linked silica. The support may be in the form of a bed, or more preferably packed in a column.

A solution of the compounds in a suitable solvent will generally be loaded on to the silica or Sephadex columns, if desired after first reducing the volume of solvent. The column may optionally be washed and then eluted with a solvent of suitable polarity. In the case of Sephadex and silica, alcohols, such as methanol; hydrocarbons, such as hexane; acetonitrile; halogenated hydrocarbons, such as chloroform or methylene chloride; or esters, such as ethyl acetate, may be used as solvents. Combinations of such solvents either alone or with water may also be used.

Elution and separation/purification of the compounds of the invention may be monitored by conventional techniques such as thin layer chromatography and high performance liquid chromatography.

Compounds of formula (II) in which $R^2$ represents a hydrogen atom or a group $OR^5$ and $R^3$ is hydrogen atom, or $R^2$ and $R^3$ together with the carbon atom to which they are attached represent $>C=O$ are either known compounds described in UK Patent Specification No. 2176182A or may be prepared from the known compounds using methods analogous to those described therein.

Compounds of formula (II) in which $R^2$ and $R^3$ together with the carbon atom to which they are attached represent $>C=CH_2$ may be prepared by reacting the corresponding known 23-keto compounds (i.e. compounds of formula (II) in which $R^2$ and $R^3$ together with the carbon atom to which they are attached represent $>C=O$) with an appropriate Wittig reagent e.g. a phosphorane of formula $(R^a)_3P=CH_2$ (where $R^a$ represents $C_{1-6}$ alkyl or aryl, e.g. monocyclic aryl such as phenyl). Suitable reaction solvents include ethers such as tetrahydrofuran or diethyl ether or dipolar aprotic solvent such as dimethyl sulphoxide. The reaction may be carried out at any suitable temperature e.g. at 0° C.

Compounds of formula (II) in which $R^2$ and $R^3$ together with the carbon atom to which they are attached represent $>C=NOR^6$ [where $R^6$ is as defined in formula (I)] may be prepared from the corresponding 23-keto compounds by reaction with a reagent $H_2NOR^6$ (where $R^6$ is as just defined).

The reaction may conveniently be effected at a temperature in the range $-20°$ to $+100°$ C., e.g. $-10°$ to $+50°$ C. It is convenient to use the reagent $H_2NOR^6$ in the form of a salt, for example an acid addition salt such as the hydrochloride. When such a salt is employed the reaction may be carried out in the presence of an acid binding agent.

Solvents which may be employed include alcohols (e.g. methanol or ethanol), amides (e.g. N,N-dimethylformamide, N,N-dimethylacetamide or hexamethlphosphoramide), ethers (e.g. cyclic ethers such as tetrahydrofuran or dioxan, and acylic ethers such as dimethoxyethane or diethyl ether), nitriles (e.g. acetonitrile), sulphones (e.g. sulpholane) and hydrocarbons such as halogenated hydrocarbons (e.g. methylene chloride), as well as mixtures of two or more such solvents. Water may also be employed as a cosolvent.

When aqueous conditions are employed the reaction may conveniently be buffered with an appropriate acid, base or buffer.

Suitable acids include mineral acids, such as hydrochloric or sulphuric acid, and carboxylic acid such as acetic acid. Suitable bases include alkali metal carbonates and bicarbonates such as sodium bicarbonate, hydroxides such as sodium hydroxide, and alkali metal carboxylates such as sodium acetate. A suitable buffer is sodium acetate/acetic acid.

The compounds of the invention may be used at levels of purity appropriate to their intended use. For use in human medicine, purities of at least 90%, preferably greater than 95%, are desirable. For veterinary or other use, lower purities will suffice, for example 50% or lower.

The invention is further illustrated by the following Examples. All temperatures are in °C. The compounds are hereinafter named by reference to the known parent "Factors", Factors A and B. Factor A is a compound of formula (II) in which $R^1$ is isopropyl, $R^2$ is hydroxy, $R^3$ is hydrogen, and $R^4$ is hydrogen and Factor B is a compound of formula (II) in which $R^1$ is methyl, $R^2$ is hydroxy, $R^3$ is hydrogen and $R^4$ is methyl. Factors A and B may be prepared as described in UK Patent Specification No. 2166436A.

EXAMPLE 1

$\Delta^{26}$- and $\Delta^{14}$-epoxide of Factor B

To a stirred and cooled (0°-5°) solution of Factor B (375 mg) in dichloromethane (10 ml) was added in one lot m-chloroperoxybenzoic acid (125 mg). After 1.5 h at 0°-5° and a further 1.5 h at room temperature the mixture was diluted with ether and the organic phase extracted with saturated aqueous sodium bicarbonate solution. Evaporation of the dried organic phase gave a gum which was separated by chromatography over Merck Kiesgel 60, 230–400 mesh silica. Elution with dichloromethane:ether (9:1) gave (after starting material) the $\Delta^{26}$-epoxide (compound of formula (I) in which $R^1$=Me, $R^2$=OH, $R^3$=H $R^4$=Me, X at 14,15-position represents a carbon-carbon bond and X at 26,27-position represents an epoxide oxygen atom) which was obtained as a white amorphous powder (43 mg) from ether-pentane. $\lambda_{max}^{EtOH}$ 244.5 nm ($\epsilon_{max}$ 50,400); $\lambda_{max}$(CHBr$_3$) 3480 (OH), 1706 cm$^{-1}$ (ester); $\delta$(CDCl$_3$) include 3.50 (s, 3H) 2.86 (s, 1H), 1.81 (s, 3H), 1.51 (s, 3H), 1.32 (d 6 Hz, 3H), 1.28 (s, 3H), 0.99 (d 7 Hz, 3H), and 0.92 (d 7 Hz, 3H). m/z=614 (M+). Further elution with the same solvent mixture afforded the $\Delta^{14}$-epoxide (compound of formula (I) in which $R^1$=Me, $R^2$=OH, $R^3$=H, $R^4$=Me, X at the 14,15-position represents an epoxide oxygen atom and X at 26,27 position represents a carbon-carbon bond) (50 mg), as an amorphous solid from ether-pentane. $\lambda_{max}^{EtOH}$ 245 nm ($\epsilon_{max}$ 27,600); $\lambda_{max}$ (CHBr$_3$) 3490 (OH), and 1708 cm$^{-1}$ (ester); $\delta$ (CDCl$_3$) include 3.52 (s, 3H), 2.62 (d 9 Hz, 1H), 1.84 (s, 3H), 1,68 (d 7 Hz, 3H), 1.63 (s, 3H), 1.25 (s, 3H), 1.02 (d 7 Hz, 3H), and 0.82 (d 7 Hz, 3H). m/z=614 (M+).

EXAMPLE 2

$\Delta^{14}$, $\Delta^{26}$ Bisepoxide and $\Delta^{14}$ and $\Delta^{26}$ Epoxides of Factor A Factor A (3.70 g) in dichloromethane (100 ml) at 4° was treated dropwise over 20 min with a solution of m-chloroperbenzoic acid (85% active, 1.23 g) in dichloromethane (30 ml). The solution was stirred for 30 minutes at 0°-5°, and for 60 min without cooling, before being left for 16 hr at 5°. This solution at 4° was treated portionwise over 50 minutes with a solution of m-chloroperbenzoic acid (0.45 g) in dichloromethane (25 ml). The solution was allowed to reach room temperature before being washed with saturated aqueous sodium bicarbonate (2×200 ml), water (150 ml) and saturated aqueous sodium chloride (150 ml). The organic phase was dried over magnesium chloride and evaporated to give a colourless solid (3.86 g). The epoxides were isolated as colourless solids after preparative reverse-phase HPLC (listed in order of decreasing polarity):

$\Delta^{14},\Delta^{26}$-bisepoxide (compound of formula (I) in which $R^1$=i-Pr, $R^2$=OH, $R^3$=H, $R^4$=H and X at the 14,15-position and at the 26,27-position represents an epoxide oxygen atom): $\lambda_{max}$ (EtOH) 245.5 nm (E$_1^1$ 446); $\delta$ (CDCl$_3$) include 5.45 (s; 1H), 4.28 (t 6; 1H), 3.96 (d 6; 1H), 2.96 (d 11; 1H), 2.66 (d 10; 1H), 2.46 (d 9; 1H), 1.86 (s; 3H), 1.31 (s; 3H), 1.20 (s; 3H), 1.10 (d 6; 3H) and 0.95 (d 7; 3H); m/z includes 644, 626, 608, 516, 498, 480, 455, 437, 399, 381, 370, 330, 281, 263, 235 and 151.

$\Delta^{14}$-epoxide (compound of formula (I) in which $R^1$=i-Pr, $R^2$=OH, $R^3$=H, $R^4$=H, X at the 14,15-position represents an epoxide oxygen atom and X at the 26,27-position represents a carbon-carbon bond): $\lambda_{max}$ (EtOH) 245.5 nm (E$_1^1$ 422); $\delta$ (CDCl$_3$) include 5.48 (s; 1H), 4.32 (t 5; 1H), 3.99 (d 6; 1H), 2.62 (d 9; 1H), 2.62 (m; 1H), 1.90 (s; 3H), 1.64 (s, 3H), 1.25 (s; 3H), 1.06 (d 6; 3H), 103 (d 6; 3H), 0.98 (d 6; 3H) and 0.81 (d 7; 3H). m/z include 628, 610, 592, 500, 482, 464, 370, 330, 247, 237, 219 and 151.

$\Delta^{26}$-epoxide (compound of formula (I) in which $R^1$=i-Pr, $R^2$=OH, $R^3$=H, $R^4$=H, X at the 14,15-position represents a carbon-carbon bond and X at the 26,27-position represents an epoxide oxygen atom): $\lambda_{max}$ (EtOH) 245.5 nm (E$_1^1$ 457); $\delta$ (CDCl$_3$) include 5.43 (s; 1H), 4.30 (t 7; 1H), 3.97 (d 6; 1H), 3.00 (d 10; 1H), 2.48 (d 8; 1H), 1.88 (s; 3H), 1.52 (s; 3H), 1.33 (s; 3H), 1.13 (d 5; 3H), 1.02 (d 6; 3H), 1.01 (d 6; 3H), and 0.98 (d 6; 3H); m/z include 628, 592, 500, 482, 464, 439, 421, 354, 313, 281, 263, 248, 235 and 151.

EXAMPLE 3

$\Delta^{14},\Delta^{26}$Bis-epoxide of Factor B

To a solution of Factor B (375 mg) in dichloromethane (1 ml) was added in a single lot m-chloroperoxybenzoic acid (250 mg). After 24 h at room temperature the mixture was diluted with ether and the organic phase then extracted with a saturated aqueous solution of sodium bicarbonate. Evaporation of the dried organic solution provided a gum which was purified by preparative HPLC using a 25×25 cm Spherosorb S5-ODS-2 column; eluting with 60% acetonitrile in water at a flow rate of 10 ml/min. The bis-epoxide (compound of formula (I) in which $R^1$=Me $R^2$=OH, $R^3$=H, $R^4$=Me and X at the 14,15-position and at the 25,26-position represents an epoxide oxygen atom) was eventually obtained as a white amorphous solid from ether-pentane, $[\alpha]_D^{23}+55°$ (c 0.76, CHCl$_3$); $\lambda_{max}$ (EtOH) 245.5 nm ($\epsilon_{max}$31,000); $\nu_{max}$ (CHBr$_3$) 3510 (OH), and 1712 cm$^{-1}$ (ester); $\delta$ (CDCl$_3$) include 5.42 (s, 1H), 4.03 (d, 5 Hz; 1H); 3.95 (m, 2H); 3.50 (s, 3H); 2.97 (d, 11 Hz; 1H); 2.89 (q, 6 Hz; 1H); 2.65 (d, 9 Hz; 1H); 182 (s, 3H); 1.33 (d, 6 Hz; 3H); 1.30 (s, 3H); 1.22 (s, 3H); 1.00 (d, 7 Hz; 3H), and 0.92 (d, 7 Hz; 3H). m/z=630(M$^+$).

The following are examples of formulations according to the invention. The term 'Active Ingredient' as used hereinafter means a compound of the invention.

Multidose parenteral injection

|  | % w/v | Range |
| --- | --- | --- |
| Active Ingredient | 4.0 | 0.1–7.5% w/v |
| Benzyl alcohol | 2.0 |  |
| Glyceryl triacetate | 30.0 |  |
| Propylene glycol to | 100.0 |  |

Dissolve the active ingredient in the benzyl alcohol and glyceryl triacetate. Add propylene glycol and make up to volume. Sterilise the product by conventional pharmaceutical methods, for example sterile filtration or by heating in an autoclave and package aseptically.

Aerosol spray

|  | % w/w | Range |
| --- | --- | --- |
| Active Ingredient | 0.1 | 0.01–2.0% w/w |
| Trichloroethane | 29.9 |  |
| Trichlorofluoromethane | 35.0 |  |
| Dichlorodifluoromethane | 35.0 |  |

Mix the Active Ingredient with trichloroethane and fill into the aerosol container. Purge the headspace with the gaseous propellant and crimp the valve into position. Fill the required weight of liquid propellant under pressure through the valve. Fit with actuators and dustcaps.

Tablet

Method of manufacture—wet granulation

|  | mg |
| --- | --- |
| Active Ingredient | 250.0 |
| Magnesium stearate | 4.5 |
| Maize starch | 22.5 |
| Sodium starch glycolate | 9.0 |
| Sodium lauryl sulphate | 4.5 |
| Microcrystalline cellulose | to tablet core weight of 450 mg |

Add sufficient quantity of a 10% starch paste to the active ingredient to produce a suitable wet mass for granulation. Prepare the granules and dry using a tray or fluid-bed drier. Sift through a seive, add the remaining ingredients and compress into tablets.

If required, film coat the tablet cores using hydroxypropylmethyl cellulose or other similar film-forming material using either an aqueous or non-aqueous solvent system. A plasticizer and suitable colour may be included in the film-coating solution.

Veterinary tablet for small/domestic animal use

Method of manufacture—dry granulation

|  | mg |
| --- | --- |
| Active Ingredient | 50.0 |
| Magnesium stearate | 7.5 |
| Microcrystalline cellulose to tablet core weight of | 75.0 |

Blend the active ingredient with the magnesium stearate and microcrystallise cellulose. Compact the blend into slugs. Break down the slugs by passing through a rotary granulator to produce free-flowing granules. Compess into tablets.

The tablet cores can then be film-coated, if desired, as described above.

Veterinary intrammary injection

|  |  | mg/dose | Range |
| --- | --- | --- | --- |
| Active Ingredient |  | 150 mg | 0.05–1.0 g |
| Polysorbate 60 | 3.0 w/w | to 3 g | to 3 or 15 g |
| White Beeswax | 6.0 w/w |  |  |
| Arachis oil | 91.0% w/w |  |  |

Heat the arachis oil, white beeswax and polysorbate 60 to 160° C. with stirring. Maintain at 160° C. for two hours and then cool to room temperature with stirring. Aseptically add the active ingredient to the vehicle and disperse using a high speed mixer. Refine by passing through a colloid mill. Aseptically fill the product into sterile plastic syringes.

Veterinary oral drench

|  | % w/v | Range |
| --- | --- | --- |
| Active Ingredient | 0.35 | 0.01–2% w/v |
| Polysorbate 85 | 5.0 |  |
| Benzyl alcohol | 3.0 |  |
| Propylene glycol | 30.0 |  |
| Phosphate buffer | as pH 6.0–6.5 |  |
| Water | to 100.0 |  |

Dissolve the active ingredient in the Polysorbate 85, benzyl alcohol and the propylene glycol. Add a proportion of the water and adjust the pH to 6.0–6.5 with phosphate buffer, if necessary. Make up to final volume with the water. Fill the product into the drench container.

Veterinary oral paste

|  | % w/w | Range |
|---|---|---|
| Active Ingredient | 7.5 | 1–30% w/w |
| Saccharin | 25.0 |  |
| Polysorbate 85 | 3.0 |  |
| Aluminum distearate | 5.0 |  |
| Fractionated coconut oil | to 100.0 |  |

Disperse the aluminium distearate in the fractionated coconut oil and polysorbate 85 by heating. Cool to room temperature and disperse the saccharin in the oily vehicle. Dispense the active ingredient in the base. Fill into plastic syringes.

Granules for veterinary in-feed administration

|  | % w/w | Range |
|---|---|---|
| Active Ingredient | 2.5 | 0.05–5% w/w |
| Calcium sulphate, hemi-hydrate | to 100.0 |  |

Blend the Active Ingredient with the calcium sulphate. Prepare the granules using a wet granulation process. Dry using a tray or fluid-bed drier. Fill into the appropriate container.

Emulsifiable Concentrate

| Active ingredient | 50 g |
|---|---|
| Anionic emulsifier | 40 g |
| (e.g. Phenyl sulphonate CALX) |  |
| Non-ionic emulsifier | 60 g |
| (e.g. Syperonic NP13) |  |
| Aromatic solvent (e.g. Solvesso 100) to 1 liter. |  |

Mix all ingredients, stir until dissolved.

Granules

| (a) | Active ingredient | 50 g |
|---|---|---|
|  | Wood resin | 40 g |
|  | Gypsm granules (20–60 mesh) to 1 kg |  |
|  | (e.g. Agsorb 100A) |  |
| (b) | Active ingredient | 50 g |
|  | Syperonic NP13 | 40 g |
|  | Gypsum granules (20–60 mesh) to 1 kg. |  |

Dissolve all ingredients in a volatile solvent e.g. methylene chloride, add to granules tumbling in mixer. Dry to remove solvent.

We claim:

1. Compounds of formula (I):

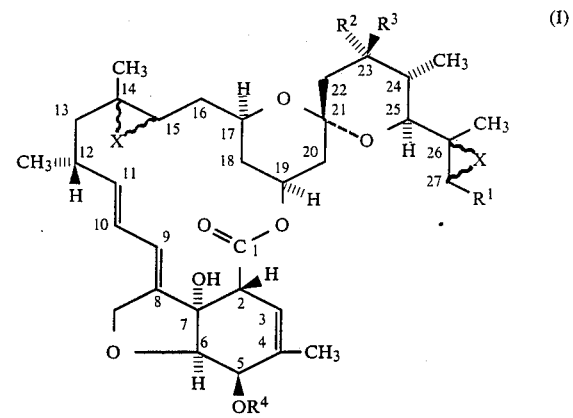

wherein
$R^1$ represents a methyl, ethyl or isopropyl group;
$R^2$ represents a hydrogen atom or a group $OR^5$ where $OR^5$ is a hydroxyl group or a substituted hydroxyl group having up to 25 carbon atoms and $R^3$ represents a hydrogen atom, or $R^2$ and $R^3$ together with carbon atom to which they are attached represent $>C=CH_2$, $>C=O$, or $>C=NOR^6$ where $R^6$ represents a hydrogen atom, a $C_{1-8}$ alkyl group or a $C_{3-8}$ alkenyl group and the group $>C=NOR^6$ is in the E configuration;
$OR^4$ is as defined above for $OR^5$;
and one of the symbols X represents an epoxide oxygen atom and the other represents an epoxide oxygen atom or a carbon-carbon bond.

2. Compounds according to claim 1 in which $R^1$ is an isopropyl group.

3. Compounds according to claim 1 in which $OR^4$ is a methoxycarbonyloxy, acetoxy, methoxy or hydroxy group.

4. Compounds according to claim 1 in which $OR^4$ is a hydroxy group.

5. A composition for use in human medicine containing an effective amount for insecticidal, acaricidal or nematodicidal purposes of at least one compound according to claim 1 together with one or more carriers.

6. A composition for use in veterinary medicine containing an effective amount for insecticidal, acaricidal or nematodicidal purposes of at least one compound according to claim 1 together with one or more carriers.

7. A pest control composition containing an effective amount for insecticial, acaricidal or nematodicidal purposes of at least one compound according to claim 1 together with one or more carriers.

8. A compound according to claim 1 where $OR^5$ is substituted hydroxy having a formula $-OCOR^7$, $OCO_2R^7$ or $-OCSOR^7$ where $R^7$ is an alkyl, alkenyl, alkynyl, cycloalkyl, aralkyl or aryl group; a formyloxy group; a group $-OR^8$ where $R^8$ is as defined above for $R^7$; a group $-OSO_2R^9$ where $R^9$ is $C_{1-4}$ alkyl or $C_{6-10}$ aryl group; a silyloxy group, a cyclic or acyclic acetaloxy group; a group $OCO(CH_2)_nCO_2R^{10}$ where $R^{10}$ is a hydrogen atom or a group as defined for $R^7$ above and n represents zero, 1 or 2; or a group $-OCONR^{11}R^{12}$ where $R^{11}$ and $R^{12}$ may each independently represent a hydrogen atom or a $C_{1-4}$ alkyl group.

* * * * *